(12) United States Patent
McVey et al.

(10) Patent No.: US 6,475,757 B2
(45) Date of Patent: Nov. 5, 2002

(54) PLASMIDS FOR CONSTRUCTION OF EUKARYOTIC VIRAL VECTORS

(75) Inventors: Duncan L. McVey, Derwood; Douglas E. Brough, Olney; Imre Kovesdi, Rockville, all of MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/905,758

(22) Filed: Jul. 13, 2001

(65) Prior Publication Data

US 2002/0004242 A1 Jan. 10, 2002

Related U.S. Application Data

(62) Division of application No. 09/513,803, filed on Feb. 25, 2000, now Pat. No. 6,329,200, which is a continuation of application No. PCT/US98/20009, filed on Sep. 23, 1998.
(60) Provisional application No. 60/059,824, filed on Sep. 23, 1997.

(51) Int. Cl.[7] .................. C12N 15/63; C12N 15/64; C12N 15/861; C12N 15/864; C12N 15/869
(52) U.S. Cl. .................. 435/91.41; 435/320.1; 435/455; 435/456; 435/5; 435/6; 435/91.4; 435/91.52; 435/91.1; 435/463
(58) Field of Search .................. 435/320.1, 455, 435/456, 5, 6, 91.4, 91.41, 91.52, 463

(56) References Cited

U.S. PATENT DOCUMENTS

| 4,769,331 A | 9/1988 | Roizman et al. |
| 5,631,153 A | 5/1997 | Capecchi et al. |
| 5,876,962 A | 3/1999 | Bishop et al. |
| 6,110,735 A | 8/2000 | Chartier et al. |
| 2001/0026794 A1 * | 10/2001 | Kovesdi et al. .......... 424/93.21 |

FOREIGN PATENT DOCUMENTS

| WO | WO89/01518 A | 2/1989 |
| WO | WO96/17070 A | 6/1996 |
| WO | WO96/25506 A | 8/1996 |
| WO | WO97/25446 A | 7/1997 |
| WO | WO98/56937 A | 12/1998 |

OTHER PUBLICATIONS

Blomfield et al., *Mol. Microbiol.*, 5 (6), 1447–1457 (Jun. 1991).
Crouzet et al., *PNAS USA, 94,* 1414–1419 (Feb. 18, 1997).

* cited by examiner

*Primary Examiner*—David Guzo
(74) *Attorney, Agent, or Firm*—Leydig, Voit & Mayer, Ltd.

(57) ABSTRACT

The present invention provides a dual selection cassette (DSC) comprising first and second DNA segments having homology to a eukaryotic viral vector, positive and negative selection genes, each operably linked to their own promoter, and one or more unique restriction enzyme sites (URES) or sitey-directed homologous recombination sites. The present invention also provides a plasmid, pN/P, comprising an independent positive selection marker gene, an origin of replication, and a dual selection cassette. The dual selection cassette and pN/P plasmid can be used to produce eukaryotic gene transfer vectors without requiring temporally-linked double recombination events or the use of specialized bacterial strains that allow the replication of plasmids comprising defective origins of replication. This method usefully increases the ratio of desired to undesired plasmid and vector constructs. Additionally, this invention provides a method for the creation of eukaryotic viral vector libraries.

11 Claims, 8 Drawing Sheets

Liberated new eukaryotic viral vector genome

PLASMIDS FOR CONSTRUCTION OF EUKARYOTIC VIRAL VECTORS

CROSS-REFERENCE TO RELATED PATENT APPLICATIONS

This patent application is a divisional of U.S. patent application Ser. No. 09/513,803, filed Feb. 25, 2000, now U.S. Pat. No. 6,329,200, which, in turn, is a continuation of International Patent Application No. PCT/US98/20009, filed Sep. 23, 1998, which designates the U.S., and which claims the benefit of U.S. patent application Ser. No. 60/059,824, filed Sep. 23, 1997.

TECHNICAL FIELD OF THE INVENTION

The present invention relates to plasmids and the use of such plasmids in the construction of eukaryotic viral vectors and the like.

BACKGROUND OF THE INVENTION

Because of their large size, many recombinant eukaryotic viruses are produced via homologous recombination. Conventionally, this homologous recombination has taken place in a host eukaryotic cell permissive for the growth of the recombinant virus (see, e.g., Berkner, *BioTechniques*, 6, 616–628 (1988)). Homologous recombination in eukaryotic cells, however, has at least two major drawbacks. The process is time consuming, and many preferred recombinant eukaryotic viral constructions have a selective disadvantage relative to the predecessor eukaryotic viruses from which they are obtained. Therefore, if a skilled artisan attempts to create a new recombinant virus through the lengthy process of homologous recombination in a eukaryotic cell and fails to create the desired virus, that artisan will not be able to readily distinguish between the need to modify the construction technique and the possibility that the virus which is sought is not viable in that cell. Accordingly, there is a need for new methods of generating eukaryotic gene transfer vectors.

Previous improvements in the generation of gene transfer vectors have included the use of yeast-based systems (Ketner et al., *Proc. Nat'l. Acad. Sci. (USA)*, 91, 6186–6190 (1994)), plasmid-based systems (Chartier et al., *J. Virol.*, 70, 4805–4810 (1996); International Patent Application WO 96/25506 (Crouzet et al.), and cosmid-based systems (Miyake et al., *Proc. Nat'l. Acad. Sci. (USA)*, 93, 1320–1324 (1996)).

The system developed by Chartier et al. includes a plasmid bearing a complete adenoviral vector genome flanked by Pac I restriction sites, which do not normally occur in the adenoviral genome. In the Chartier et al. method, adenoviral sequences contained on a linear DNA are homologously recombined in vivo into a linearized vector comprising a left and right ITR. The resultant vector is propagated, isolated, and digested with Pac I, and the restriction fragment bearing the adenoviral vector is transfected into a mammalian cell that is permissive for replication of the virus. The Chartier et al. method provides relatively pure sources of adenoviral vector sequences. Unfortunately, the Chartier et al. method lacks a powerful, positive means of self-selecting the desired products and lacks flexibility in the way novel vectors can be produced.

International Patent Application WO 96/25506 (the '506 application, Crouzet et al.) discloses the use of a two plasmid system with selective pressure mechanisms that enable the production of plasmids comprising adenoviral vectors flanked by unique restriction sites. Compared to other prior art methods, the '506 method is in some ways better suited for the production of eukaryotic viral vectors. For example, the '506 method does not require that two homologous recombination events occur simultaneously or virtually simultaneously (as does the Chartier et al. method). This temporal separation of the recombination events results in an increased opportunity to obtain both recombination steps in the vector production process. However, in order to reduce the "background" of undesired homologous recombination products, the '506 system requires and employs a specialized bacterial strain. This specialized strain contains a DNA polymerase defect such that normal plasmid origins of replication will not function in the strain. However, only one such strain is described in '506. Use of the '506 method without the specialized strain and modified origin of replication leaves the skilled artisan with a difficult screening task, which is so substantial as to negate its improvements over the Chartier et al. method. Thus, the '506 method lacks flexibility.

Systems described in the prior art can expedite the production of new recombinant eukaryotic viruses; however, additional flexibility and selection pressures are desired. Accordingly, the present invention provides an efficient and flexible method of preparing eukaryotic viral vectors, as well as vectors useful in practicing these methods. These and other advantages of the present invention, as well as additional inventive features, will be apparent from the description of the invention provided herein.

BRIEF SUMMARY OF THE INVENTION

The present invention provides a dual selection cassette (DSC) comprising first and second DNA segments having homology to a eukaryotic viral vector, and positive and negative selection genes, each operably linked to their own promoter. The present invention also provides a plasmid, pN/P, comprising an independent positive selection marker gene, origin of replication, a dual selection cassette, and at least one of the following: one or more unique restriction enzyme sites (URES), one or more flanking site-directed homologous recombination sites, or a phage packaging site. The dual selection cassette and pN/P plasmid can be used to produce eukaryotic gene transfer vectors without requiring temporally-linked double recombination events or the use of specialized bacterial strains that allow the replication of plasmids comprising conditional origins of replication. This method usefully increases the ratio of desired to undesired plasmid and vector constructs. The present invention also provides a method for construction of a library comprising or consisting of a multiplicity of the present inventive vectors comprising a multiplicity of genetic elements that may be the same or different and are assembled simultaneously in a single reaction. The features of these nucleic acids and this method allow the generation and use of eukaryotic expression libraries in the study of functional genomics and the like.

The invention may best be understood with reference to the accompanying drawings and in the following detailed description of the preferred embodiments.

DESCRIPTION OF THE PREFERRED EMBODIMENTS

The pN/P Plasmid

The present invention provides a plasmid, pN/P (FIG. 1), which is useful in the construction of eukaryotic viral vectors and the like. The plasmid pN/P is a circular DNA containing an independent first positive selection marker gene, an origin of replication, a dual selection cassette (DSC), and an element selected from the group consisting of (a) one or more (e.g., two) site-directed homologous recombination system DNA binding sites (e.g., ψRec sites; present in pN/P1), (b) one or more (e.g., two) restriction enzyme sites (e.g., pRESs; present in pN/P2) distinct from that of the dual selection cassette (if the DSC comprises a URES), and (c) at least one phage packaging site (see, e.g., pN/Pφ). The pN/P plasmid can be used for rapidly making a large set of related viral vectors, wherein each vector of the set comprises a new viral or passenger gene that replaces the DSC of a viral vector carried by pN/P.

The Positive Selection Marker Gene

The first independent positive selection marker gene of pN/P (hereinafter "first marker gene") is any gene carried by a circular DNA that will confer a growth advantage to a bacterium carrying a plasmid comprising the gene under a particular and known condition. The first marker gene is distinct from the positive selection gene of the DSC (hereinafter "positive selection gene"), described below, and is used to maintain pN/P in a replicating bacterial host. Common examples of genes suitable for use as the first marker gene comprise auxotrophy complementing genes and antibiotic resistance genes such as the beta-lactamase gene (which confers resistance to ampicillin), the chloramphenicol acetyl transferase gene (which confers resistance to chloramphenicol), and the kanamycin resistance gene (illustrated in FIG. 2).

The Origin of Replication

Figure 3:
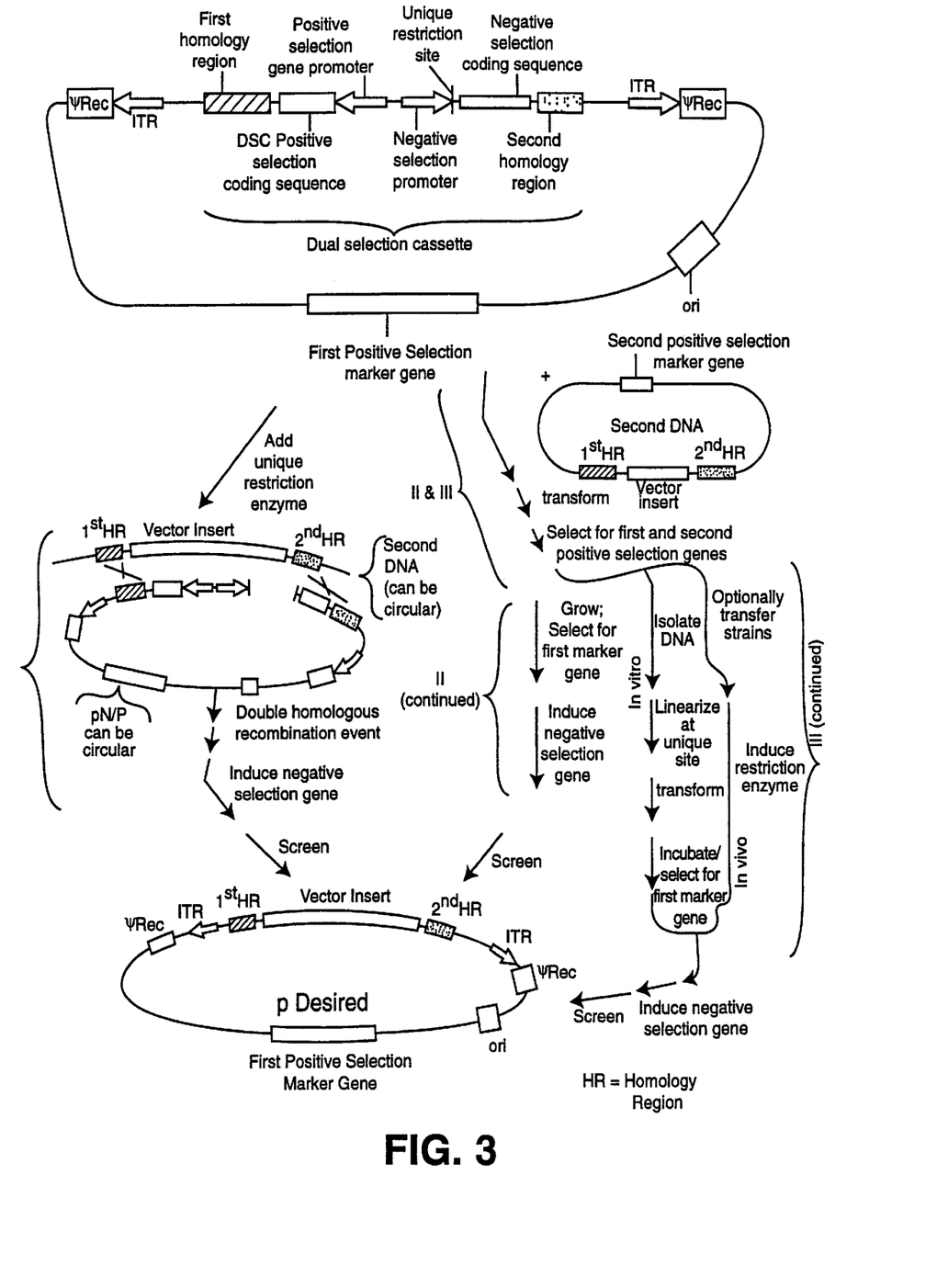
FIG. 3 illustrates three processes by which pN/P can be used to generate a plasmid (pDesired) comprising a desired eukaryotic viral vector.

The origin of replication of pN/P can be any origin of replication. If pN/P is a particularly large plasmid or comprises highly toxic sequences, then it can be preferable for the origin of replication to support a low copy number of the plasmid in the cell to enhance the maintenance of the pN/P plasmid in the cell. Additionally, pN/P can be used in a homologous recombination event with a second plasmid (i.e., a second DNA). The homologous recombination event is designed to transfer the negative selection gene from the DSC to the second DNA thereby producing a second DNA by-product as well as the product, pDesired. It is necessary for at least one cell comprising pDesired to not have the second DNA by-product, so that, when the negative selection is substantially active, cells containing pDesired are produced. Therefore, the origin of replication of pN/P should be the same, or otherwise incompatible with, an origin of replication carried by the second DNA in either method II or III (as depicted in FIG. 3 and discussed in detail below).

Alternatively, the origin of replication of the donor plasmid can be a conditional origin of replication.

The Dual Selection Cassette

The dual selection cassette (DSC) contains at least six genetic elements (or functional DNA segments) which can (but need not) overlap each other and include (i) a first and (ii) a second viral vector homology region, (iii) a DNA encoding a negative selection gene product that is operably linked to (iv) a negative selection gene promoter, and (v) a positive selection gene that is operably linked to (vi) a positive selection gene promoter. A DNA encoding a selection gene product in operable linkage with its selection promoter is called a selection gene (for the purposes of the present invention).

The identity of the first and second homology regions are independently selected, and are of sufficient size and homology so as to enable a homologous recombination event with a eukaryotic viral vector, or an analogue thereof, such that a desired region of a virus, viral vector, or analogue thereof, is replaced (or modified) as a result of the homologous recombination event as described below. The first and second homology regions are separated by the negative and positive selection genes of the DSC. Additionally, if pN/P comprises one or more viral ITRs, either or both of the homology regions can comprise an ITR, or portion thereof. In the virus, viral vector, or analogue thereof that will recombine with the DSC, the DNA that is homologous to the first and second homology regions can be contiguous or can be separated by an intervening DNA segment. (It will also be appreciated that many embodiments of viral vectors comprise heterologous passenger genes or heterologous DNA segments and that these heterologous passenger genes or DNA segments can be utilized in the homologous recombination reaction described in this paragraph.)

In the context of the present invention, a negative selection gene product is any RNA or protein that can confer a strong growth disadvantage to a host expressing it, preferably causing the death of a host expressing it, under appropriate conditions. The negative selection gene is used to "drive" the reaction process forward (i.e., to select for desirable vector constructs and cause the elimination of undesirable vector constructs). Suitable negative selection genes include, but are not limited to, NP-1, sacB, ccd genes (e.g., ccdB), a tetracycline resistance gene (tet$^R$), par genes (e.g., parD), and Kid. Suitable negative selection genes also include fusion proteins of these genes (e.g., genes comprising portions of these genes fused to portions of the genes encoding thioredoxin, β-galactosidase, the OmpA signal sequence, luciferase, protein A or any other suitable fusion partner). Suitable negative selection genes also include active variants of the aforementioned genes, which can comprise deletions, mutations, or other modifications. In short, a suitable negative selection gene provides for the death or substantial decrease in the growth rate of a bacterium expressing the same. A discussion of negative selection genes can be found in *Escherichia coli and Salmonella*, ch. 22, at 2317, 2318 (Niedhardt ed., 2d ed. 1996).

By way of further illustration and not limitation, it is noted that the DNA encoding an OmpA FLAG/NP-1 fusion protein is illustrative of an negative selection gene that is useful in the present invention. The OmpA FLAG/NP-1 gene product is a rat defensin fusion protein that lacks its cognate signal sequence and further comprises the OmpA signal sequence. Production of an OmpA FLAG/NP-1 fusion protein in a bacterium renders that bacterium nonviable. While not intending to be bound by any particular theory, one explanation for the negative selection action of OmpA FLAG/NP-1 is that the OmpA signal localizes the NP-1 portion of the protein in, or proximally to, a bacterial membrane such that the NP-1 portion of the protein forms pores in that membrane and destroys the host cell's viability.

The sacB gene, while not preferred in the present invention, is illustrative of another negative selection gene. The sacB gene-product converts sucrose (when present in the growth medium) to leaven, which is highly toxic to bacteria. The sacB negative selection gene can be regulated by providing or withholding sucrose from a bacterial host that constitutively expresses sacB.

The negative selection gene promoter can be strongly regulable (i.e., inducible, suppressible, or both inducible and suppressible) so as to provide control over the negative selection pressure that the negative selection gene exerts. Alternatively, if the negative selection gene promoter is not regulable, then a suitable means for preventing the function of the negative selection gene must be used. Suitable means for controlling the function of the negative selection gene include, but are not limited to, withholding or providing a substrate which the negative selection gene converts into a toxic product (e.g., sucrose for the sacB gene) or providing in trans a powerful regulator of the negative selection gene product. The Tac promoter (a Trp and lac hybrid promoter), which is repressible by the lac I protein and inducible by IPTG, is illustrative of a suitable negative selection gene promoter in the context of the present invention. To achieve a sufficient level of control over the Tac promoter it is preferable to use this promoter in combination with a bacterial strain that expresses the repressor protein, such as a lac strain, preferably a lac $I^Q$ strain, or a bacterial strain with a plasmid expressing the lac repressor protein. Inclusion of a lac $I^Q$ gene in pN/P facilitates insertion of the DSC in the E3 and E4 regions.

Figure 2:
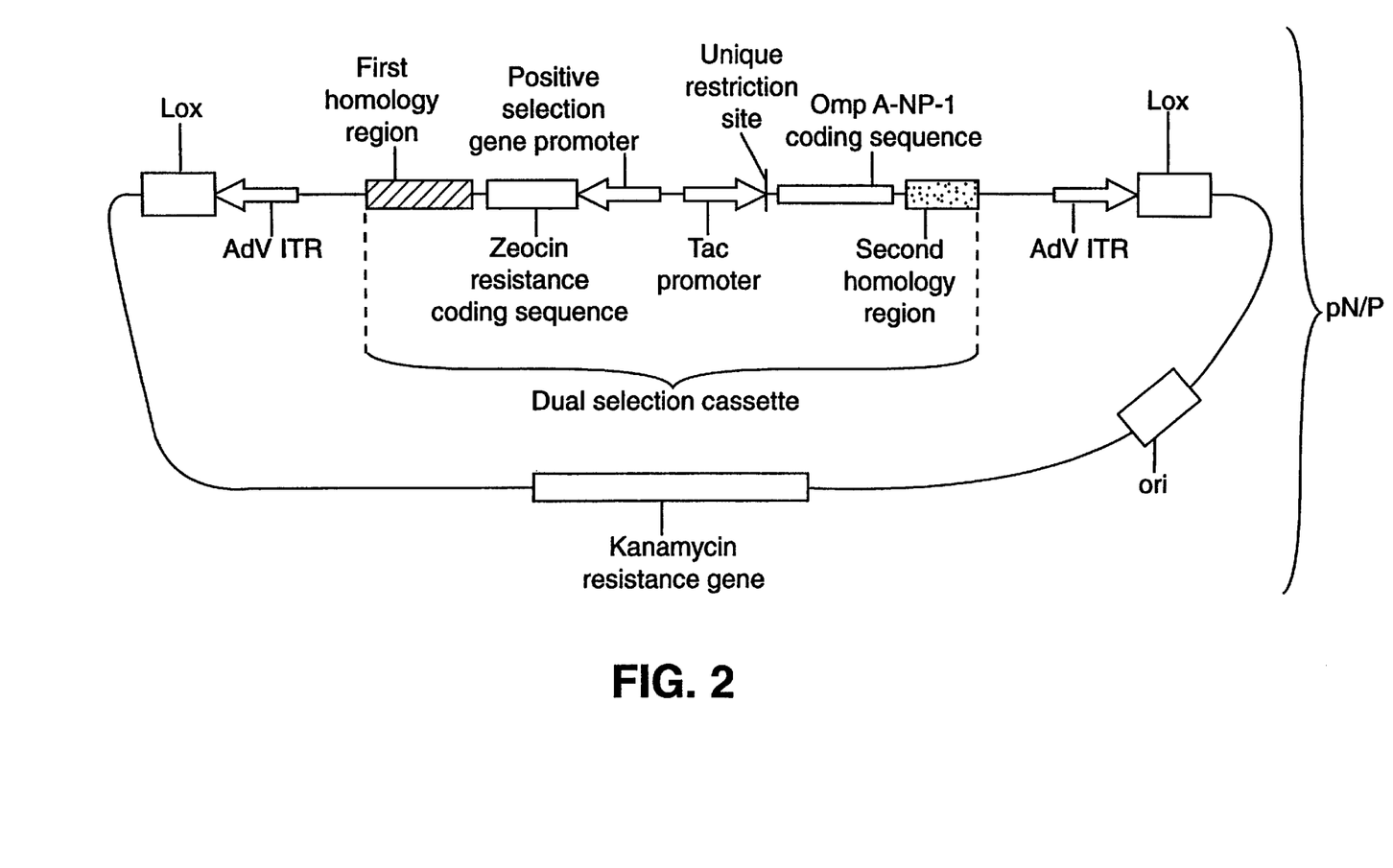
FIG. 2 depicts an embodiment of the pN/P plasmid comprising some preferred elements.

The positive selection gene of the DSC is preferably distinct from the first marker gene; however, genes suitable for use as a first marker gene are also suitable for use as a positive selection gene of the dual selection cassette. The zeocin resistance gene, ble, is depicted in FIG. 2 as the positive selection gene of the DSC. The positive selection gene is physically close (i.e., proximal) to the negative selection gene. Therefore, these genes are genetically linked and selective pressure for retention of the positive selection gene will tend to apply selective pressure against the loss of the negative selection gene (when the negative selection gene is inactive, of course).

The positive selection gene promoter can be any suitable promoter, but it will be appreciated that a constitutive promoter is preferable for many embodiments of the present invention, at least inasmuch as the artisan then need not attend to the function of the positive selection gene promoter.

Figure 1:
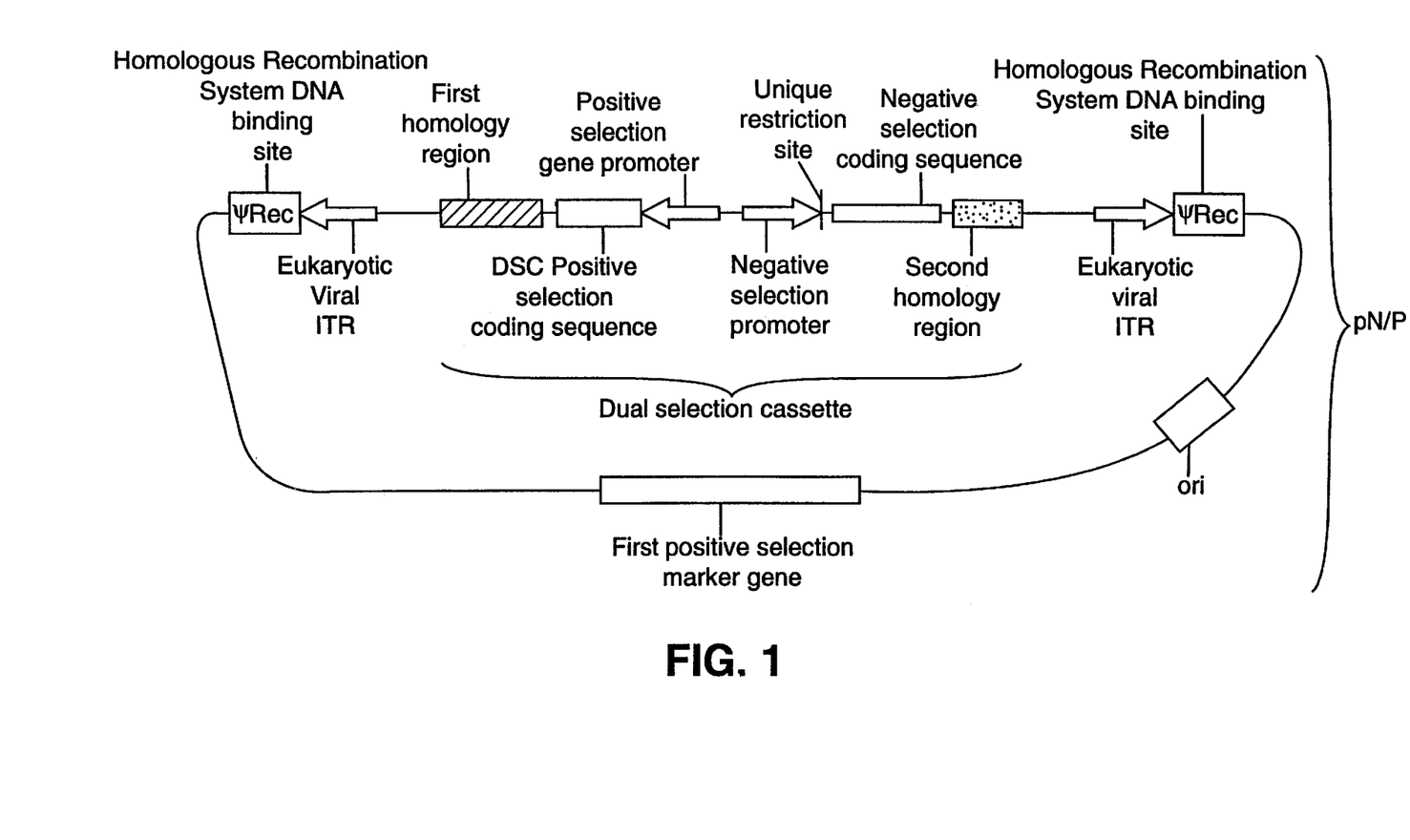
FIG. 1 depicts an embodiment of the plasmid pN/P.

The positive selection gene promoter is preferably positioned and/or oriented so that it does not promote transcription of an RNA encoding the negative selection gene product (i.e., does not promote transcription of a sense-strand RNA of the negative selection gene). As depicted in FIG. 1, this can be accomplished by placing the positive and negative gene promoters in a 5' to 5' (or back to back) orientation, such that transcription starts at each promoter and proceeds away from the other.

Optionally, a single gene can function as both a positive and negative selection gene, depending upon the promoter. For example, a DSC comprising an EM-7 promoter and encoding a zeocin resistance protein or encoding a lacZ-zeocin resistance fusion protein can be incorporated into the present inventive vector. The DNA fragment comprising the EM-7 promoter actually contains two promoters. One promoter is a constitutive promoter recognized by bacterial host cell polymerases. Embedded within the DNA fragment comprising the EM-7 promoter is a T7 promoter, which is recognized only by T7 RNA polymerase. In a cell lacking T7 RNA polymerase, there is a strong positive selective pressure in the presence of zeocin or zeocin analogues. Thus, the gene is functioning as a positive selection gene. However, in a cell expressing T7 RNA polymerase, the cell grows very slowly or dies. T7 polymerase can be constitutively or inductively expressed from the bacterial genome or a plasmid in the cell, or can be provided by superinfection with a phage. In the presence of T7 polymerase, the gene is functioning as a negative selection gene. Thus, this DSC can be used to select for cells by adding zeocin or a zeocin analogue to the growth medium and can be used to antiselect for cells by ensuring that T7 RNA polymerase is expressed in the cells.

While not wishing to be bound by any particular theory, it is believed that stringent RNA polymerases (e.g., T7), have a substantially higher affinity for nucleotides than host RNA polymerases. When the T7 RNA polymerase directs the expression of the DSC the host cell's metabolic processes are so depleted that the growth rate of the cell is severely attenuated. This action appears to be much stronger when the RNA transcript of the T7 polymerase directs the translation of a substantial open reading frame (ORF)(at least about 15 amino acids in length, but preferably greater than about 30 or 100 amino acids in length) and when the ORF is preceded by a Shine-Dalgarno sequence.

Figure 7:
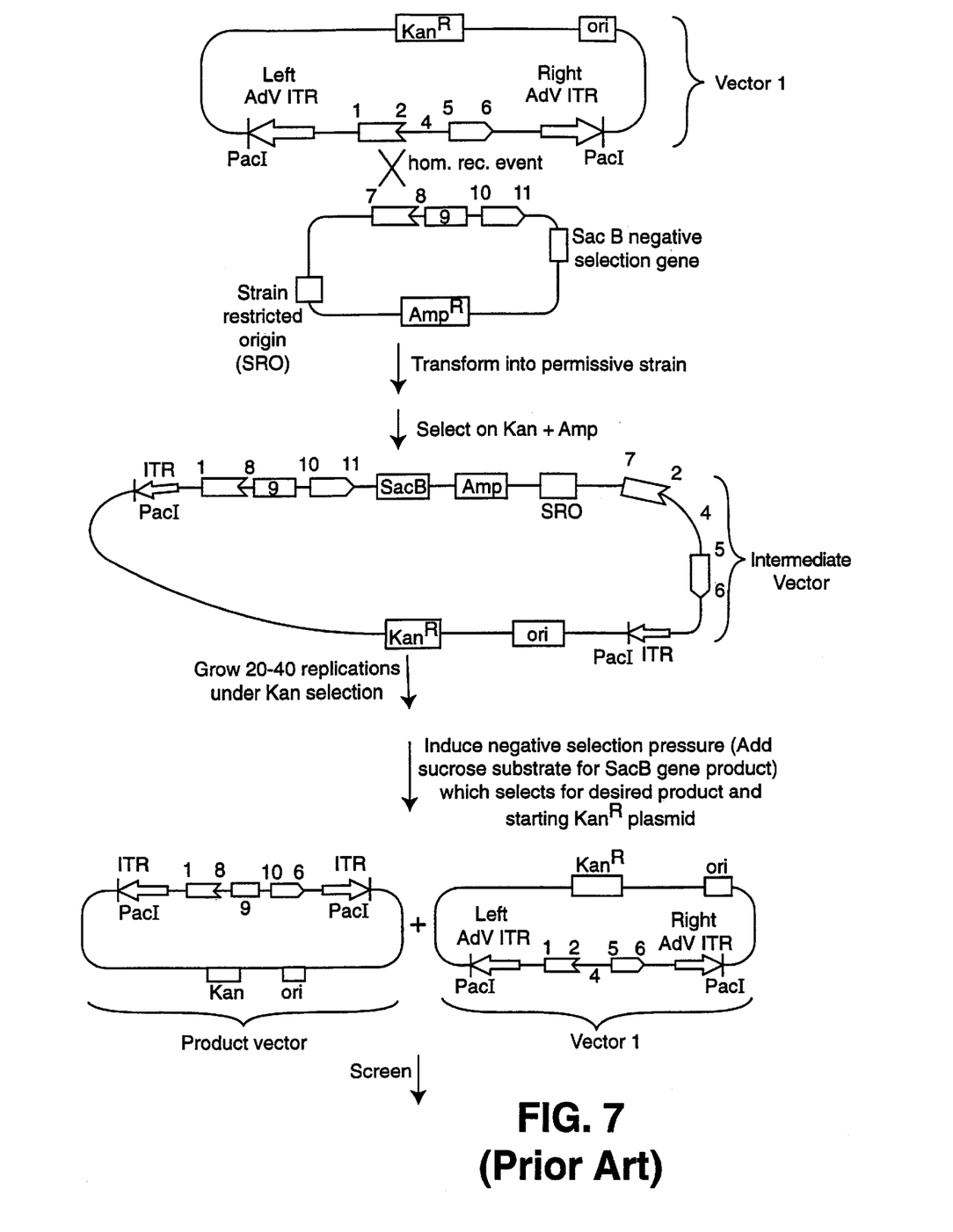
FIG. 7 depicts a prior art method of producing adenoviral vectors in bacteria.

The dual selection cassette also optimally comprises a unique restriction enzyme site (URES). Cleavage of the DNA at the URES substantially attenuates or eliminates the negative selection pressure provided by the negative selection gene (when the bacterium containing the DSC is placed in conditions in which the negative selection gene or gene product is active). This modification of the pN/P plasmid allows the artisan to utilize homologous recombination to rapidly generate a eukaryotic viral gene transfer vector, without reliance on bacterial strains comprising mutations in their DNA polymerases (as is required in the prior art method depicted in FIG. 7). Rather, use of the pN/P plasmid comprising a URES in the DSC allows the skilled artisan to utilize virtually any bacterial strain and the specialized genetic features each of these strains have to offer.

One preferred placement of the URES of the DSC is between the negative selection gene promoter and the negative selection gene, such that, when pN/P is cut at the unique restriction site contained in the dual selection cassette, the negative selection gene is operably disconnected from its promoter. When OmpA/NP-1 is used as the negative selection gene, the unique restriction site can also be placed between the DNA encoding the OmpA signal sequence and the DNA encoding the NP-1 polypeptide or protein, so that when the restriction site is cut the resultant gene product will not exert negative selection pressure on the host bacterium. One skilled in the art will appreciate that a wide variety of suitable equivalent URES placements exist and can readily identify many of these based on the context of the actual negative selection gene employed in any particular embodiment. It also is permissible to have more than one occurrence of the URES in the DSC for any particular embodiment of the present invention (e.g., both before and after the negative selection gene promoter).

pN/P preferably contains at least one, and more preferably at least two, eukaryotic viral ITRs (as is depicted in FIG. 1). One or both of the ITRs can, but need not, form a portion of the dual selection cassette. One embodiment of pN/P is pN/P1. pN/P1 comprises one or more ψRec sites located at the termini of the DSC and any other viral vector elements present in pN/P which will eventually be represented in the product gene transfer vector.

For convenience, the following definitions apply to pN/P plasmids including pN/P1 and pN/P2 (for the purposes of the present invention). A DNA segment is defined to be contained on the plasmid segment of pN/P if it is on the portion of the DNA containing the origin of replication and the independent first positive selection gene marker. A DNA segment is defined to be on the viral segment of pN/P if it is on the remaining DNA segment. Of the elements recited above, only the first marker gene and origin of replication are carried on the plasmid fragment, the other elements are on the viral fragment of pN/P.

The ψRec sites of pN/P1 can be placed in any orientation. If there are two ψRec sites which are parallel, then when the circular DNA is contacted with a suitable site-directed homologous recombination a second and a third (smaller) circular DNA is obtained from pN/P, or a suitable variant of pN/P.

Silenced Dual Selection Cassettes

In some embodiments of the present invention, it is desirable to conditionally prevent the operation of the negative selection gene of the DSC by a method other than removal of an essential element of the negative gene or by the uncoupling (e.g., by restriction digestion) of the promoter and the DNA encoding the gene product. A dual selection cassette containing a conditionally silenced negative selection gene is a conditionally silenced DSC. If it is desirable to perform manipulations of a plasmid comprising a DSC in a cell incapable or temporally incapable of adequately supressing the negative selection gene promoter, then use of a conditionally silenced DSC is advantageous.

Figure 8:
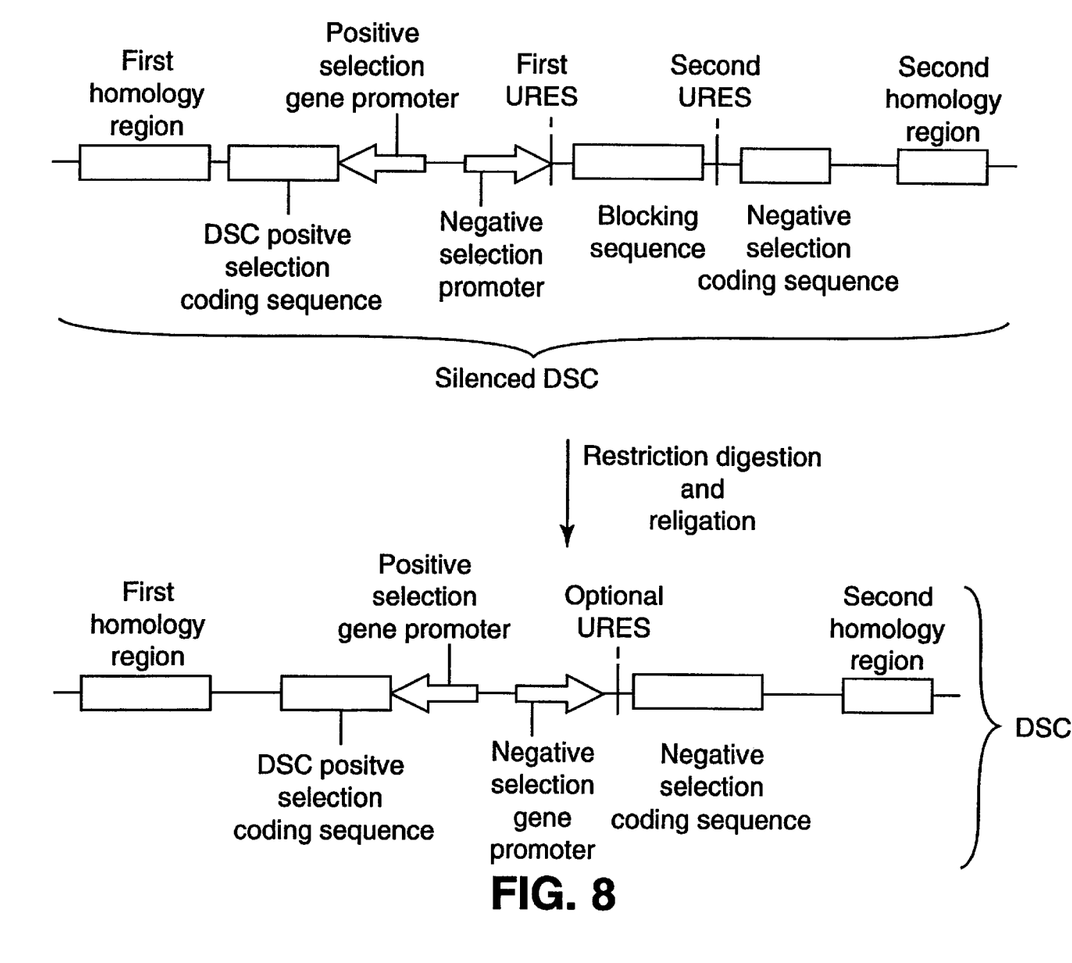
FIG. 8 depicts an embodiment of pN/P wherein the negative selection gene is conditionally silenced.

A conditionally silenced DSC can be generated, inter alia, by inserting a transcription blocking sequence or a translational missense generating sequence between a pair of URESs located in the DSC between the negative selection gene promoter and the DNA encoding the negative selection gene product (see, e.g., FIG. 8). For example, a DSC can contain a translational missense generating blocking sequence flanked by a first and second unique restriction enzyme site (the first and second URESs in this embodiment can, but need not, be identical or isoschizomers). In this case, the blocking sequence is placed downstream of the Shine-Dalgarno sequence (or its equivalent) and upstream of the translation initiation codon of the DNA encoding the negative selection gene product such that translation (protein synthesis) is initiated in the blocking sequence and is in an alternative reading frame other than the open reading frame of the DNA encoding the negative selection gene product. Preferably, the reading frame of the blocking sequence is selected such that a translation termination codon does not precede the cognate translation initiation site of the DNA encoding the negative selection gene product. Thus, unintended transcription from the negative selection gene promoter results in a protein product other than the negative selection gene product.

An alternative blocking sequence is a Rho dependent (or other) transcription termination sequence. Thus, a reasonable level of initiation of transcription from the negative selection gene promoter is terminated before the production of the negative selection gene product, protecting the cell harboring the silenced DSC from the lethal effects of the negative selection gene.

It is preferable that the URESs flanking the blocking sequence generate compatible cohesive ends such that the silenced DSC can be readily converted into an active DSC by restriction digestion and re-ligation, which results in the loss of the blocking sequence. Of course, the skilled artisan will appreciate that a multiplicity of silencing sequences can be inserted into the DSC so that the negative selection gene can be silenced by a second mechanism, independent of the mechanism which is used to regulate the DSC, that does not comprise a blocking sequence.

When the blocking sequence of the silenced DSC is removed the negative selection gene can become active. That is, the negative selection gene product can be produced. Of course, removal of the blocking sequence does not preclude regulation of the negative selection gene promoter, non-supply of a substrate for the negative selection gene product or other means of controlling the negative selection gene.

ψRec Sites of pN/P1

The ψRec sites are any suitable site-directed homologous recombination DNA binding sites. The ψRec sites are preferably lox sites. Other suitable ψRec sites include, for example, the FRT sites of the FLP-FRT system and Rs sites of the R-Rs system.

Restriction Enzyme Sites of pN/P2

Another embodiment of pN/P is pN/P2, which is a pN/P plasmid wherein the ψRec sites of pN/P1 are replaced by one or more restriction enzyme sites (pRESs) that preferably are different than the URES of the DSC, if the DSC comprises a URES and preferably is not contained in the viral fragment of pDesired. Conveniently, if there are two restriction sites (i.e., a pair), they can be the same so that a single restriction enzyme can entirely liberate the viral vector from a pDesired plasmid made from pN/P2, although it will be readily appreciated that these sites can also be different. Pac I is illustrative of one type of URES that is frequently suitable for use in pN/P2. For the sake of simplicity, pN/P will be used to refer to both pN/P1 and pN/P2, unless otherwise explicitly stated.

The plasmid pN/P2B is a further embodiment of pN/P2. In pN/P2B one or both of the first and second homology regions of the DSC comprises an ITR. Additionally, a restriction enzyme site (i.e., a URES) that can be cleaved by a restriction enzyme that does not cut within the DSC, or within the viral fragment of a particular pDesired plasmid made using pN/P2B, is located in a position suitably proximal to the ITR of the first or second homology region, at opposite termini of the DSC. In this embodiment, a pDesired plasmid can be generated in accordance with the methodology set forth in FIG. 3, cut with an enzyme specific for the URES, and transfected into a eukaryotic cell that is permissive for the growth of the viral vector contained in pDesired. Because the restriction digest renders the ITR suitably proximal (i.e., within about 2000 bp, preferably within about 300 bp, more preferably within about 100 bp, most preferably within about 35 bp) to the terminus of the DNA, the viral vector is able to replicate.

Phage Packaging Sites pN/Pφ

Another embodiment of pN/P is pN/Pφ. pN/Pφ comprises a phage packaging site (e.g., a lambda cos site or a phage P1 packaging site) on the plasmid fragment of pN/P, which allows the production of cosmid libraries and the like. Many phage packaging processes linearize the DNA to be encapsidated at, or very near, the phage packaging sequence. Additionally, if an ITR of a viral genome (e.g., an adenoviral genome) is suitably proximal (i.e., within about 2000 bp, preferably within about 300 bp, more preferably within about 100 bp, most preferably within about 35 bp) to a terminus of that DNA, it can mediate the initiation of replication of that viral genome (or viral vector DNA) in a permissive cell, even if the opposite ITR is not suitably proximal to a terminus. Therefore, the phage packaging site is preferably (suitably) proximal to an ITR of a viral vector contained in pN/Pφ.

pN/Pφ can be processed into pDesired (see FIG. 3), and this pDesired plasmid (conveniently referred to as pDesired-φ) can be incubated in a cell or extract capable of encapsidating appropriately sized DNAs into a phage capsid. The encapsidated pDesired-φ can then be directly transfected into eukaryotic cells, particularly in vitro. Of course, the phage-like particles containing the linearized pDesired-φ can also be extracted to yield uncoated pDesired-φ, and this uncoated pDesired-φ can also be used to transfect target cells in any suitable manner known in the art. Thus, use of an encapsidation site present in pN/Pφ allows the rapid generation of eukaryotic viral vectors in pDesired that are directly useable, particularly in vitro.

pDesired-φ can also be packaged in a phage capsid that comprises a modified coat protein. Modified coat proteins, similar to those described in U.S. Pat. No. 5,559,099 (Wickham et al.), U.S. Pat. No. 5,712,136 (Wickham et al.), International Patent Application WO 98/07877 (GenVec, Inc.), International Patent Application WO 98/07865 (GenVec, Inc.), and International Patent Application WO 97/20051 (GenVec, Inc.) can direct the targeting of the pDesired/phage particle to a target cell (e.g., one found in or obtained from a eukaryotic organism (e.g., a human)).

For example, the gene encoding the D protein of lambda can be modified by inserting DNA encoding for an amino acid sequence specific for a cell surface structure, a receptor (including cell surface liposaccharides and the like), an antibody, or an epitope at the amino and/or carboxyl terminus (i.e., within about 10, and preferably within about 3, amino acids of either terminus). Alternatively, the lambda D coat protein can be chemically (i.e., covalently) or transiently (e.g., noncovalently) modified by a bispecific molecule having affinity for a lambda coat protein and (i) a cell surface structure, (ii) a receptor (including cell surface liposaccharides and the like), (iii) an antibody, or (iv) an epitope. This modified D protein can then be used to prepare a pDesired-φ encapsidated in a re-targeted lambda capsid.

Modification of a T7 packaging system is also useful in the context of the present invention. In this example, the protein product of a recombinant T7 gene 10 that encodes a carboxy-terminally modified protein 10, or a carboxy-terminal modified wild type protein 10, can be used in a T7 packaging extract to prepare a pDesired-φ encapsidated in a re-targeted T7 capsid.

pDesired-φ packaged in wild type or modified phage capsids can be used to deliver transgenes to target cells. The packaged pDesired-φ is contacted to a eukaryotic cell. The eukaryotic cell internalizes the encapsidated pDesired-φ. Through this internalization process, the encapsidated DNA becomes substantially free of the capsid proteins that surround it, so that each gene of the pDesired-φ that is capable of being expressed in the target eukaryotic cell can be transcribed and translated and the viral vector can replicate. Preferably, the targeted pDesired-φ phage is internalized with an endosomolytic agent so that the endosomolytic agent ruptures the endosomes containing the agent and the pDesired-φ. It is known that such rupture significantly increases the efficiency of expression of the gene transfer vector. Examples of endosomolytic agents useful in the context of the present invention include chloroquine, calcium phosphate particles, adenoviral coat proteins (including adenoviral virions), and adeno-associated viral coat proteins (including AAV virions).

Figure 4:
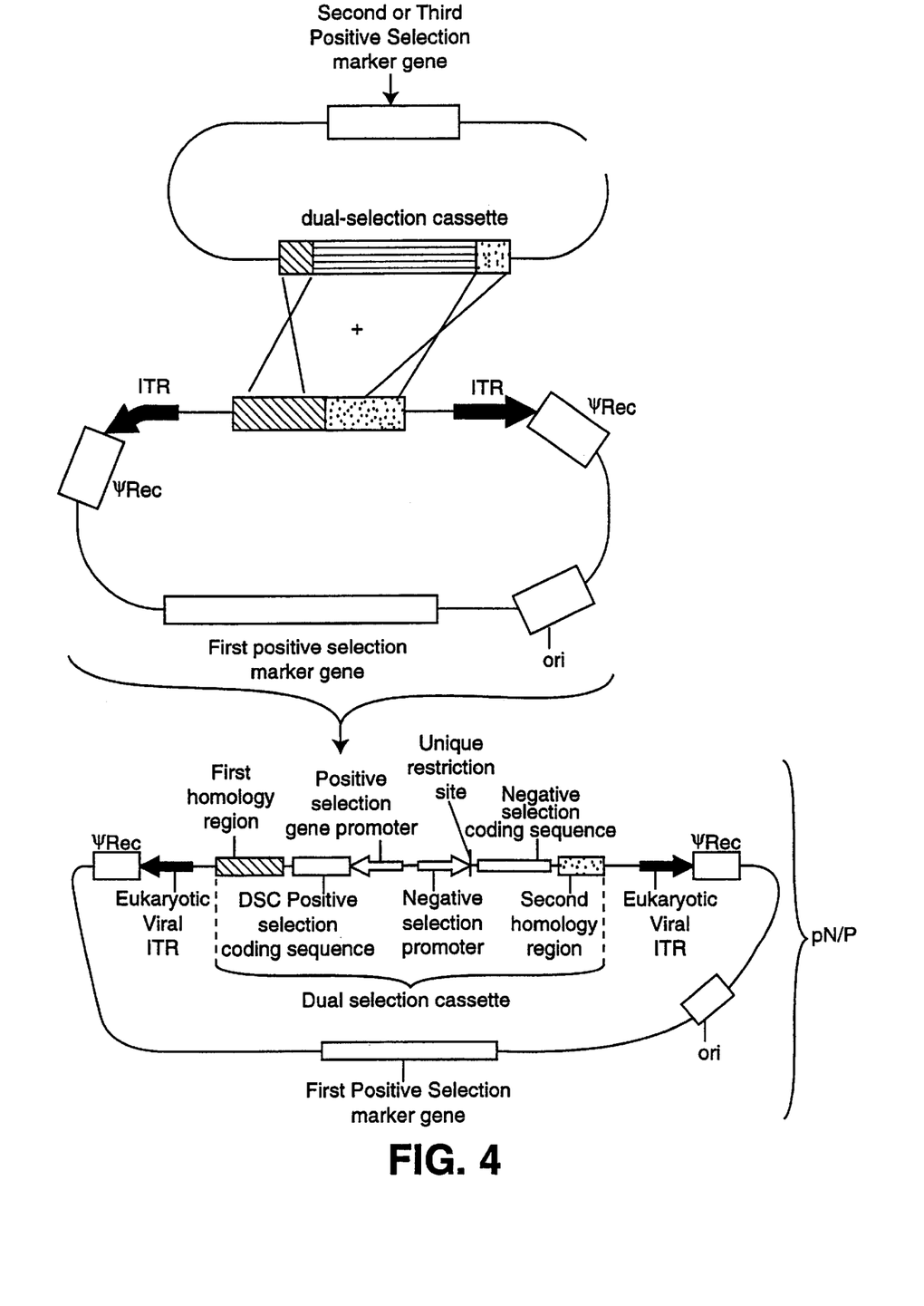
FIG. 4 illustrates one process by which pN/P can be generated.

Synthesis of pN/P Plasmids pN/P can be generated by any suitable means. One method of generating pN/P makes use of double recombination between a so-called recipient viral plasmid and a so-called dual selection cassette donor plasmid (see FIG. 4). The recipient viral plasmid comprises a first marker gene, ψRec or URES sites, and one or more segments of DNA having high homology with a eukaryotic virus. If the pN/P product plasmid is also to contain the optional eukaryotic viral ITRs, then the recipient viral plasmid also frequently contains these ITRs. The optional ITRs and the DNA having homology to a eukaryotic virus are positioned in the recipient viral plasmid on the DNA segment defined by the ψRec sites and opposite of the independent positive selection marker gene.

The dual selection cassette donor plasmid comprises a dual selection cassette, which optimally comprises each of the six genetic elements defined above. Often the dual selection cassette is identical to the dual selection cassette that ultimately will reside in the desired pN/P plasmid. A preferred method is for the viral recipient plasmid to be circular while the DSC donor plasmid is linear.

Following transfection and a dual recombination event, colonies comprising the desired pN/P plasmid can be selected according to their resistance to both the independent positive selection marker gene of pN/P and the positive selection gene of the dual selection cassette. Thus, bacterial colonies comprising the desired pN/P plasmid can be readily identified, allowing use of the product pN/P plasmid. Additionally, it will be appreciated that there are many other ways to generate additional embodiments of the pN/P plasmid, such as by the homologous recombination of two pre-existing pN/P plasmid embodiments or the like, and by routine molecular biology methods, including ligation of restriction digest products, and site-directed or regional-specific mutagenesis of pN/P plasmids or other plasmids.

Of course, one skilled in the art will appreciate that there exists a multiplicity of techniques to obtain a particular desired pN/P plasmid. Therefore, the foregoing discussion of the synthesis of a pN/P plasmid is meant to illustrate the invention, and is not intended to limit in any way the scope of the invention.

Use of pN/P Plasmids

Any particular pN/P vector of the present invention can be utilized in accordance with one or more of the following general methods (see FIG. 3).

The first method ("Method I" of FIG. 3) comprises linearizing pN/P with a restriction enzyme that cuts the unique restriction enzyme site within the dual selection cassette. A second DNA (linear or circular) comprising DNA segments with high homology to the first and second homology regions is co-transformed with the linearized pN/P vector into a bacterial host. In one embodiment, pN/P is not subjected to the restriction digestion, but rather is left as a circular plasmid while the second DNA is linear. Following transfection of the DNAs into the bacterial host, enzymes provided by the host mediate two homologous recombination events. In another embodiment, the second DNA is linear and ligated into pN/P at a unique restriction site, rather than homologously recombined into the plasmid.

The host is then maintained for a suitable period of time (e.g., 2–24 hours) under conditions that are selective for the first positive selection marker gene of the dual selection cassette. Thereafter, the transformed bacterial host is grown under conditions such that the negative selection gene promoter becomes active (i.e., the negative selection gene promoter is induced and/or derepressed, or, alternatively, when a constitutive promoter is used for the negative selection gene promoter, a substrate for the negative selection gene product is added to the growth medium or substrate). Individual viable cells are then isolated, propagated, and screened for the desired vector, pDesired. The plasmid pDesired essentially is a pN/P vector that has homologously recombined with the second DNA in such a fashion as to contain a desired eukaryotic viral construct. Identifying individual cell isolates comprising pDesired by standard techniques is vastly simplified in comparison to prior art techniques (for constructing and identifying a desired construct), because in the inventive method the resultant bacterial colonies must harbor the positive selection gene and must not harbor the negative selection gene of the dual selection cassette.

The second and third general methods ("Method II" and "Method III", respectively, of FIG. 3) for utilizing pN/P begin in similar ways and comprise transfecting pN/P along with a second DNA (in the second method the second DNA can be linear, but is preferably circular). The second DNA (as depicted in FIG. 3) comprises a second positive selection marker gene (e.g., an ampicillin resistance gene) which is distinct from that carried by pN/P and the positive selection gene of the DSC. A bacterial host is co-transformed by the two plasmids and propagated under conditions that are selective for both the first (of pN/P) and second (of the second DNA vector) positive selection marker genes (e.g., in the presence of kanamycin and ampicillin). Two recombination products are most likely to result from the multiplicity of possible recombination events possible at this point. First, a relatively rare double recombination event utilizing both the first and second homology regions can occur to produce the desired vector. Second, and more likely, a single recombination event can occur giving rise to a single vector comprising both starting vectors. Without directly screening for colonies comprising the desired construct (e.g., by PCR analysis or colony lift), those bacteria comprising the desired construct can be selected through use of suitable growth conditions. A transformed culture then is allowed to incubate for a suitable period of time during which mitosis and recombination events occur. At this point, the second and third general methods diverge.

The second method relies primarily on a double recombination event to produce pDesired. The resultant plasmid products of the double recombination event include pDesired and a new plasmid which comprises the negative selection gene promoter and gene. Accordingly, the bacterial culture is expanded (or doubled) a suitable number of generations so that pDesired will reside in, or segregate into, a cell that does not comprise a plasmid comprising an active negative selection gene promoter and gene. This expansion is done under conditions which select for the first positive selection marker gene (i.e., selection for pN/P and pDesired), but not the second positive selection marker gene (not selecting for the donor plasmid). The minimum number of average doublings used to segregate the plasmids can be as low as about 1, but is preferably about 20. The maximum number of doublings is preferably about 40, but can be as many as 200 or more. Once pDesired has been allowed to segregate into cells that are free of plasmids comprising a negative selection gene promoter and gene, the negative selection gene is induced, and surviving cells are isolated (e.g., plated for colonies). The isolates that grow up under these conditions have a high likelihood of containing the desired product vector (pDesired) and, therefore, are readily and efficiently screened for the presence of pDesired.

The third method does not rely on initially obtaining a double recombination event, but instead takes advantage of the more frequently produced single recombination event. The plasmid intermediate of this single recombination event (as well as other plasmids) is propagated without a requirement for screening. The propagated vectors, including the desired intermediate vector, then are linearized at the unique restriction enzyme recognition site contained in the dual selection cassette.

The restriction digestion can take place either in vivo or in vitro (in which case it is possible to also phosphatase the vector to inhibit re-ligation). If an in vivo restriction digest reaction is used, the plasmids can be co-transformed into a cell that constitutively expresses the unique restriction enzyme, or, alternatively, a bacterial host can be used which regulatably expresses the enzyme that cuts the unique restriction site.

After cutting the URES, the third method is continued by incubating the linearized plasmid in a bacterial cell under conditions selective for the first positive selection marker gene and making the negative selection gene active. It will be appreciated that a bacterial cell will not survive under these conditions unless it comprises a circularized plasmid comprising the first positive selection marker gene and does not contain an active negative selection gene promoter and gene. This is most frequently accomplished by the second homologous recombination event that is required to produce pDesired.

Even though a substantial fraction of the linearized pN/P plasmid will be re-ligated by bacterial enzymes, cells comprising these "contaminants" are eliminated because they repair the defect introduced into the negative selection gene promoter and gene by the restriction digestion.

Homologous recombination reactions have a relatively low frequency of occurrence and lead to a multiplicity of reaction products. The third method usefully reduces this inefficiency by temporally separating each of the two recombination events required to produce pDesired. Further, homologous recombination is a reversible process which can lead to the accumulation of reactants at the expense of products. All three methods select against cells harboring plasmids resulting from reversed homologous recombination or harboring unreacted plasmids by simultaneously requiring the presence of the first positive selection marker gene and the absence of an active negative selection gene promoter and gene.

Selection of Second DNAs For Use With pN/P

In each of the three foregoing methods a second DNA is inserted into a particular pN/P vector. In another preferred embodiment, the pN/P comprises a eukaryotic viral vector which further comprises the dual selection cassette. This embodiment provides for a passenger gene or a new viral gene to be engineered into the portion of the vector that is occupied by the dual selection cassette. To accomplish this result, the second DNA can comprise a promoter that is functional in an intended target cell of the eukaryotic viral vector that is obtained from pDesired. The functional promoter is operably linked to the passenger or new viral gene. Alternatively, the passenger gene can be inserted into the vector such that it comes under control of such a promoter that pre-exists in the viral vector (see, e.g., the embodiment wherein one of the two homology regions of the DSC is a promoter or comprises a portion of a functional promoter). Of course, the passenger gene can be any gene encoding an RNA or protein of interest to the skilled artisan. Therapeutic genes, genes encoding a protein that is to be studied in vitro and/or in vivo, genes encoding catalytic RNAs, genes encoding anti-sense RNAs, and modified viral genes are illustrative of possible passenger genes of interest.

A viral vector library containing a multiplicity of passenger genes can also be obtained. The library can also be made through the use of cosmid cloning of an intermediate vector generated by homologous recombination. The library consists of a multiplicity of genetic elements that may be the same or different and are assembled simultaneously in a single reaction. It will be appreciated that these libraries have a multiplicity of utilities including, but not limited to, the study of functional genomics (e.g., identifying the functions and identities of genomic and complementary DNA sequences), viral vector design, structure-function studies of individual genes or gene products.

In the second DNA, the passenger gene with or without a promoter is flanked by a first and a second homology region selected according to the desired design of the eukaryotic viral vector. That is, the first homology region is homologous to a region of the eukaryotic viral vector to the left side of the passenger gene, and the second homology region is homologous to a region to the right side of the passenger gene. Therefore, upon double recombination of the second DNA with the pN/P plasmid at the first and second homology regions, all the viral vector sequences between the first and second homology recombining regions are removed from the vector, including the dual selection cassette comprising the negative selection gene.

It will be appreciated that portions of the negative and (especially) the positive selection genes can constitute a portion of the first and/or second homology region. Thus, the entire dual selection cassette need not necessarily be recombined out of pN/P in the production of pDesired. Additionally, it will be appreciated that DNA segments distal to the dual selection cassette can be used as first and/or second homology regions (e.g., the ITRs of an adenovirus can serve as the first and second homology regions for homologous recombination with a pN/P plasmid comprising an adenoviral vector that further comprises a dual selection cassette in the E2A region of the adenoviral genome). In this embodiment, a eukaryotic viral replicon, wherein all viral sequences not comprising the ITRs are eliminated from the vector by recombination with the second DNA, is created. Of course, the replicon can be created such that it also comprises a viral packaging site, such that the replicon can be packaged in a solution (in vitro) or cell (in vivo) comprising the necessary packaging components. Thus, the homologous recombination between pN/P and the second DNA also can be used to simultaneously insert sequences into a eukaryotic viral vector and form a deletion in the eukaryotic viral vector.

Use of pDesired

Figure 5:
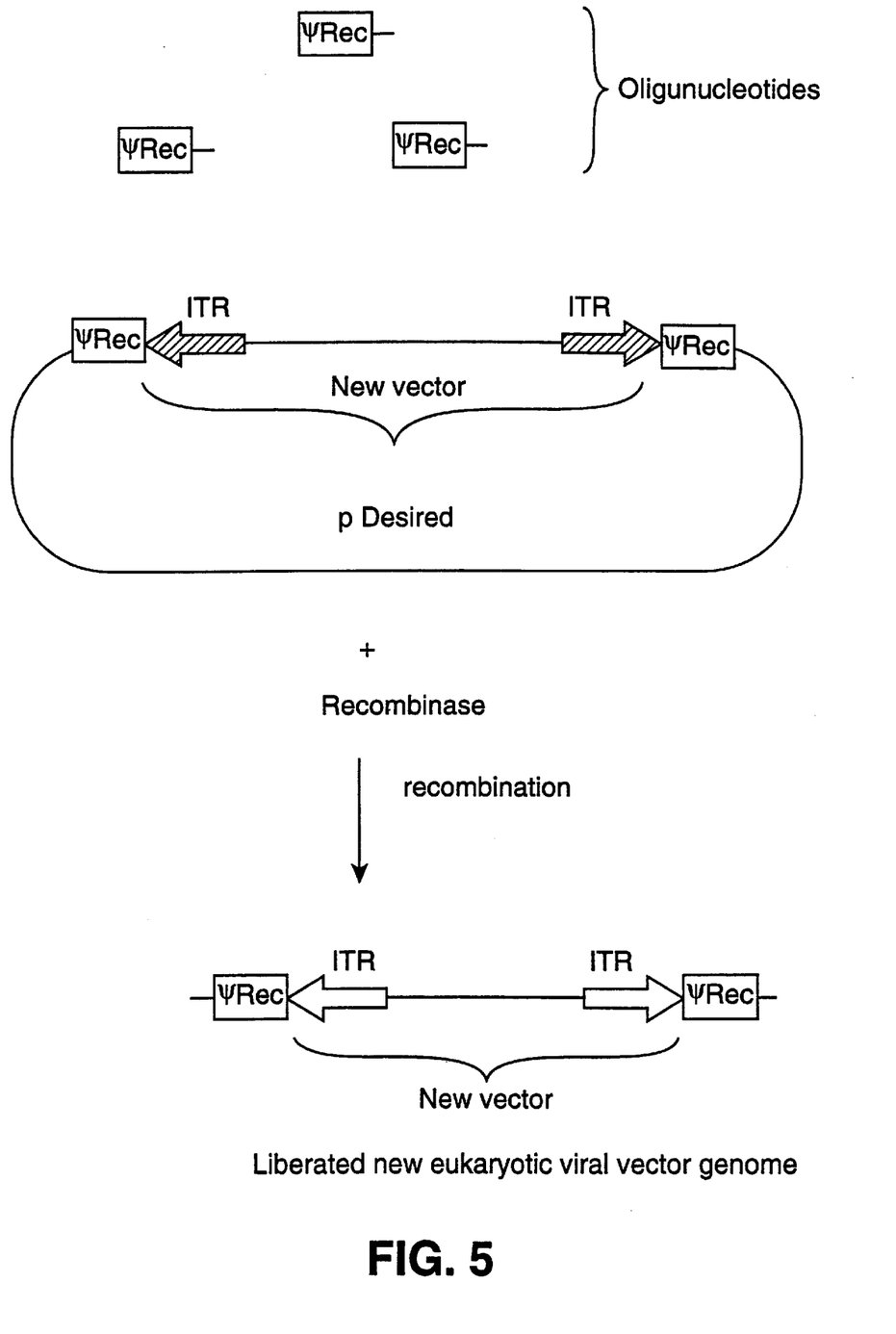
FIG. 5 depicts one process by which a desired eukaryotic viral vector can be liberated from pDesired, when pDesired is produced in part from pN/P1 (described below).
Figure 6:
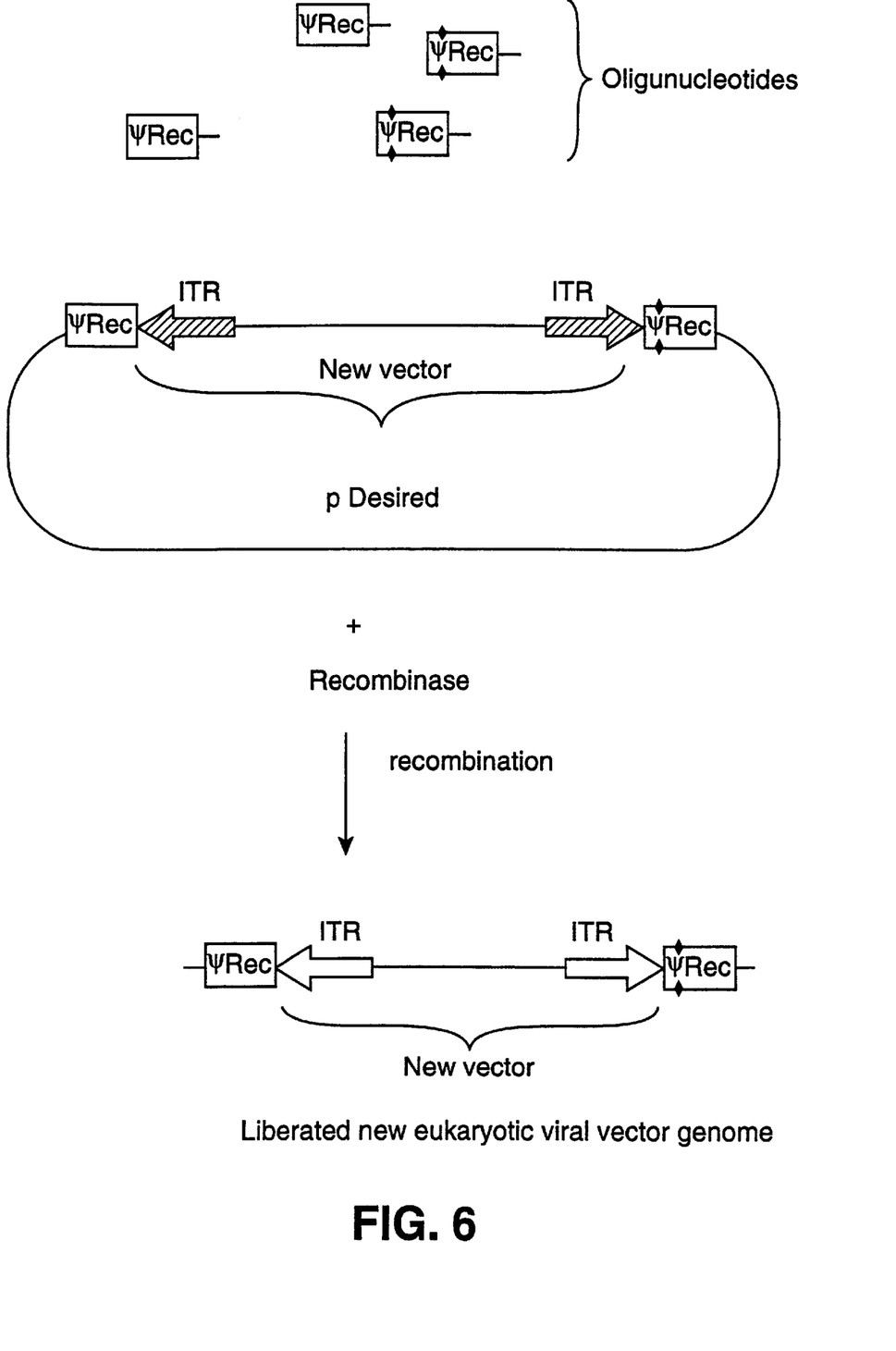
FIG. 6 depicts an alternative process by which a desired viral vector can be liberated from pDesired when pDesired is produced in part from pN/P1.

The desired plasmid, pDesired, can be obtained by any suitable method, such as any of the above three methods utilizing pN/P, or by any suitable variation of these general methods. The eukaryotic viral vectors contained in these plasmids can replicate in a permissive eukaryotic cell if at least one of the ITRs is suitably proximal (within about 2000 bp, preferably about 300 bp, more preferably within about 100 bp, most preferably within about 35 bp) to a free terminus of the DNA. Such a free terminus can be established by cutting with a restriction enzyme if a suitable restriction site is available and contact with the restriction enzyme does not completely disrupt the viral vector (as is the case wherein pN/P2 is used to form pDesired). Alternatively, functional eukaryotic viral genomes can be isolated from pDesired by placing pDesired in a solution (in vitro) or cell (in vivo) comprising an appropriate recombinase (e.g., Cre) and oligonucleotides containing at least one suitable ψRec site (e.g., a lox site). The recombinase reaction (e.g., Cre-lox) yields a eukaryotic viral vector with terminally proximal ITRs (i.e., within about 2000 bp of either terminus, preferably about 300 bp, more preferably within about 100 bp, most preferably within about 35 bp); see FIG. 5). The recombinase reaction can be carried out in vitro or in vivo. The system can be provided with further flexibility if the two depicted ψRec sites are both functional, but incompatible (such sites are known in the art; see also FIG. 6). The recombinant eukaryotic viral vector so produced can be transfected into a permissive eukaryotic cell and is able to replicate in such cells. The eukaryotic viral vectors comprised by pDesired are able to transfer passenger genes to target cells in vivo or in vitro.

The following examples further illustrate the present invention but, of course, should not be construed as in any way limiting its scope.

EXAMPLES

Example 1

This example illustrates a preferred method of generating pN/P. This method is preferred because it produces a relatively large number of colonies containing pN/P.

This method utilized a double homologous recombination between the recipient viral plasmid and the dual selection cassette donor plasmid. The recipient viral plasmid contained a suitable positive selection gene, i.e., a kanamycin resistance gene, and a suitable origin of replication, i.e., a p15 origin of replication. In addition, the recipient plasmid contained two segments homologous to the two regions of the DSC having high homology with a eukaryotic virus. The DSC donor plasmid contained a distinct positive selection gene, i.e., an ampicillin resistance gene, and the dual selection cassette.

Recombination was carried out under various conditions: (1) 4 ng of cut recipient viral plasmid was combined with 3 ng of cut DSC donor plasmid; (2) 40 ng of cut recipient plasmid was combined with 30 ng of cut donor plasmid; (3) 4 ng of uncut recipient plasmid was combined with 3 ng of cut donor plasmid; (4) 4 ng of uncut recipient plasmid was combined with 30 ng of cut donor plasmid; (5) 4 ng of uncut recipient plasmid was combined with 6 ng of uncut donor plasmid; and (6) 4 ng of uncut recipient plasmid was combined with 60 ng of uncut donor plasmid. Each recombination was carried out in a transformation volume of 50 μl. The results of the various recombinations are set forth in Table 1 below.

TABLE 1

| Recombination Reaction | 1 | 2 | 3 | 4 | 5 | 6 |
| --- | --- | --- | --- | --- | --- | --- |
| Recipient viral plasmid | | | | | | |
| pAdE1(Z) - cut | 4 ng | 40 ng | — | — | — | — |
| pAdE1(Z) - uncut | — | — | 4 ng | 4 ng | 4 ng | 4 ng |
| DSC donor plasmid | | | | | | |
| AdE1(DSC) - cut | 3 ng | 30 ng | 3 ng | 30 ng | — | — |
| AdE1(DSC) - uncut | — | — | — | — | 6 ng | 60 ng |
| Result | | | | | | |
| no. of colonies | 0 | 2 | 0 | 26 | 0 | 29 |
| % positive | — | 50% | — | 85% | — | 0% |
| no. of positive colonies | — | 1 | — | 22 | — | 0 |

As is apparent from the data in Table 1, low concentrations of cut or uncut recipient plasmid in conjunction with low concentrations of cut or uncut donor plasmid did not produce any colonies (see recombination reactions 1, 3, and 5). In contrast, a high concentration of cut recipient plasmid, as well as a low concentration of uncut recipient plasmid, in conjunction with a high concentration of cut donor plasmid produced 2 and 26 colonies respectively, some of which were positive, i.e., colonies containing pN/P (see recombination reactions 2 and 4). While a low concentration of uncut recipient plasmid in conjunction with a high concentration of uncut donor plasmid produced 29 colonies, none of these colonies were positive, i.e., colonies containing pN/P (see recombination reaction 6).

The preferred conditions for generation of pN/P are a low concentration of uncut recipient viral plasmid and a high concentration of cut DSC donor plasmid. Under these conditions, a total of 26 colonies were produced. Eighty-five percent of these colonies were positive, resulting in a total of 22 colonies containing pN/P (see recombination reaction 4). The other combinations of recipient and donor plasmid did not produce substantial numbers of positive colonies.

EXAMPLE 2

This example illustrates the use of one embodiment of pN/P to generate adenoviral vectors deficient in one or more essential gene functions of the E1 and E4 regions of the adenoviral genome. The adenoviral vector produced in the present example is also deficient in the E3 region of the adenoviral genome.

A variant of a serotype 5 adenovirus, AdE1/IX(B/N)E3(10)E4(BgGus), is cloned into the publicly available pACYC177 (New England BioLabs) between the Ban I and Drd I sites, which destroys the ampicillin resistance gene, but leaves the p15 origin or replication and kanamycin resistance genes intact. AdE1/IX(B/N)E3(10)E4(BgGus) comprises the wild type sequences of Ad5 except for sequences 356–4120 (E1-IX; which deletes the E1 and pIX regions of the adenoviral genome), 28592–30470 (E3; the result of a Xba I digestion that precludes the expression of region E3 gene products), and 32832–35564 (E4). A dual selection cassette comprising a constitutively expressed (i.e., an EM-7 promoter) ble gene (zeocin resistance) and a Tac promoter (i.e., a Trp/lac hybrid promoter that is IPTG regulable) drives the expression of an OmpA/Flag/NP-1 chimeric gene in the opposite direction as the ble gene. A unique Swa I site resides between the Tac promoter and the chimeric gene. The deleted sequences in the E4 region are replaced by (from right to left) the human beta-globin polyadenylation sequence, the coding sequence for β-glucuronidase, and the SV40 early polyadenylation sequence. The β-glucuronidase gene is oriented 3'–5' with respect to the Adenovirus genome. The two polyadenylation sequences flanking the β-glucuronidase gene precludes expression of the β-glucuronidase gene.

The pN/P construct can then be modified to contain any desired passenger gene. Two suitable passenger genes are the $VEGF_{121}$ or iNOS cDNAs under the control of a CMV immediate early promoter and an SV40 polyadenylation sequence.

To enable that result, the $VEGF_{121}$, and iNOS coding sequences were cloned between the CMV promoter and SV40 early polyadenylation signal in a plasmid that also contains Ad5 sequences 1–355 and 3333–5792 on opposite sides of the expression signals. The CMV promoter is adjacent to the Ad5 coordinate 3333 and drives expression leftward relative to the Ad5 sequences so that the expression cassettes will point to the left with respect to the adenoviral vector generated below. The plasmid is also modified, if necessary (as in pGEM2) to contain suitable restriction sites, such as Asc I and Pac I and comprises an ampicillin resistance gene.

The pN/P plasmid described above and at least one of the plasmids comprising $VEGF_{121}$ or iNOS described above are transformed into a suitable bacterial strain, such as BJ5183 (courtesy of Dr. Douglas Hanahan, University of Calif., San Francisco), BJ5183 is reportedly a RecBC sbc, laq $I^Q$ bacterial strain. The transformed BJ5183 is grown on medium containing glucose, kanamycin, and zeocin. A small scale plasmid preparation (e.g., miniprep) is performed. The resultant combined plasmid preparation is digested with Swa I which separates the Tac promoter from the chimeric NP-1 gene. The linearized DNA is transformed into a second bacterial strain (which can, but need not, be different from the first strain) and grown on media containing kanamycin and glucose overnight at a suitable temperature and level of aeration. The following day the cells are concentrated by light centrifugation, washed in glucose and antibiotic free growth medium, and plated on a third growth medium (solid phase) lacking glucose and comprising IPTG and kanamycin. The resultant colonies are screened using standard techniques for the desired construct. The plasmid from at least one colony that comprises a desired construct is isolated. The DNA is linearized, such that, at least one of the two adenoviral ITRs is proximal to a terminus of the DNA, and transfected into 293/ORF6 cells. The transfected cells are plated into 100 mm tissue culture dishes.

The transfection is passaged on 293/ORF6 cells to amplify the adenoviral vector. The amplified adenoviral vector is then liberated from the cells by cellular disruption (e.g., freeze-thaw lysis), and the cellular debris is pelleted by centrifugation. The resultant supernatant fluid constitutes a new adenoviral vector comprising a desired transgene in the E1 region of the adenoviral genome and deficiencies in the E3 region and all the essential gene functions of the E1 and E4 region.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of making a viral vector, said method comprising (a) transfecting a cell with a first DNA and a second DNA, wherein said first DNA comprises a DNA segment that is homologous to a DNA segment in said second DNA such that homologous recombination occurs to produce an intermediate vector comprising a phage packaging site and a eukaryotic viral vector, and (b) ligating one or more linear third DNA(s) into said intermediate vector to produce said viral vector.

2. The method of claim 1, wherein said method further comprises (a') propagating said intermediate vector in bacteria, and (a") linearizing a portion of the stock of intermediate vector.

3. The method of claim 1, wherein said method further comprises (c) packaging said viral vector into a phage capsid.

4. The method of claim 1, wherein said intermediate vector is linearized in a region comprising said eukaryotic viral vector.

5. The method of claim 1, wherein said linear third DNA is ligated into a region comprising said eukaryotic viral sector.

6. The method of claim 1, wherein said intermediate vector is selected from a group consisting of an adenoviral vector, an adenoviral-associated vector, and a herpes viral vector.

7. The method of claim 1, wherein said phage packaging site is a cos packaging site.

8. The method of claim 1, wherein said method comprises ligating multiple linear third DNAs into said intermediate vector to produce said viral vector, wherein said multiple linear third DNAs are the same or different and are obtained from a population of DNA comprising a multiplicity of genetic elements.

9. The method of claim 2, wherein the method further comprises (c) packaging said viral vector into a phage capsid.

10. The method of claim 2, wherein the method comprises ligating multiple linear third DNAs into said intermediate vector to produce said viral vector, wherein the multiple linear third DNAs are the same or different and are obtained from a population of DNA comprising a multiplicity of genetic elements.

11. The method of claim 3, wherein the method comprises ligating multiple linear third DNAs into said intermediate vector to produce said viral vector, wherein the multiple linear third DNAs are the same or different and are obtained from a population of DNA comprising a multiplicity of genetic elements.

* * * * *